(12) United States Patent
Wu (10) Patent No.: US 10,125,340 B2
(45) Date of Patent: Nov. 13, 2018

(54) PHOTOBIOREACTOR SYSTEMS AND METHODS FOR PRODUCING BIOMASS

(71) Applicant: Xiaoxi Wu, Encinitas, CA (US)

(72) Inventor: Xiaoxi Wu, Encinitas, CA (US)

( * ) Notice: Subject to any disclaimer, the term of this patent is extended or adjusted under 35 U.S.C. 154(b) by 0 days.

(21) Appl. No.: 14/795,647

(22) Filed: Jul. 9, 2015

(65) Prior Publication Data
US 2016/0010044 A1 Jan. 14, 2016

Related U.S. Application Data

(60) Provisional application No. 62/023,636, filed on Jul. 11, 2014.

(51) Int. Cl.
| | |
|---|---|
| *C12N 1/00* | (2006.01) |
| *C12N 1/12* | (2006.01) |
| *C12M 1/00* | (2006.01) |
| *C12M 1/09* | (2006.01) |
| *C12M 1/02* | (2006.01) |
| *C12M 1/12* | (2006.01) |

(52) U.S. Cl.
CPC ............ *C12M 21/02* (2013.01); *C12M 23/22* (2013.01); *C12M 23/56* (2013.01); *C12M 27/00* (2013.01); *C12M 37/00* (2013.01); *C12N 1/12* (2013.01)

(58) Field of Classification Search
CPC .......... C12M 21/02; C12M 23/56; C12N 1/12
See application file for complete search history.

(56) References Cited

U.S. PATENT DOCUMENTS

| | | | | |
|---|---|---|---|---|
| 8,033,047 B2 * | 10/2011 | Rasmussen | ............ | A01G 33/00 435/292.1 |
| 2009/0130706 A1 * | 5/2009 | Berzin | ................... | C12M 21/02 435/41 |
| 2011/0129906 A1 * | 6/2011 | Edelson | ................ | C12M 21/02 435/257.1 |

FOREIGN PATENT DOCUMENTS

| | | |
|---|---|---|
| CL | 201102912 | 3/2012 |
| DE | 10 2009 016 738 A1 | 10/2010 |
| WO | WO 2008/134010 A2 | 11/2008 |
| WO | WO 2013/088407 A1 | 6/2013 |
| WO | WO2014064602 * 5/2014 | ............... G01L 1/14 |

OTHER PUBLICATIONS

Polzin et al. "Halogenated Monoterpene Production by Microplantlets of the Marine Red Alga Ochtodes secundiramea Within an Airlift Photobioreactor Under Nutrient Medium Perfusion" Biotechnology and Bioengineering, vol. 82, No. 4, May 20, 2003.*
Bruinsma, Jelle, "The Resource Outlook to 2050: By How Much Do Land, Water and Crop Yields Need to Increase by 2050?"; FAO Expert Meeting, Jun. 24-26, 2009, Rome.
Burlew, John S., "Algal Culture: From Laboratory to Pilot Plant." Carnegie Institution of Washington Publication 600. Washington, D.C., 1961.
Sheehan, John, et al., "A Look Back at the U.S. Department of Energy's Aquatic Species Program—Biodiesel from Algae", Jul. 1998.
DOE NAABB Algal Biofuel Consortium Program, 2010-2013.
Dirks, Gary, et al., "2015 DOE BETO Algae Platform Review", Mar. 25, 2015.
Hames, Molly, "Funding Opportunity Announcement Number: DE-FOA-0000615. Advancements in Sustainable Algal Production (ASAP)", Feb. 2012.
Flikinger, Michael C., Upstream Industrial Biotechnology, vol. 1-2, 2013.
Pulz O. and Scheibenbogen K. "Photobioreactors: Design and Performance with Respect to Light Energy Input", Advances in Biochemical Engineering/Biotechnology, 59:pp. 123-152, 2006—Abstract.
Richmond, Amos, ed. Handbook of Microalgal Culture—Biotechnology and Applied Phycology, Blackwell Publishing, Oxford, UK, 2004—Sample.
International Search Report, dated Oct. 6, 2015.
Chilean Office action dated Aug. 13, 2018 in connection with Application No. 00056-2017.

* cited by examiner

*Primary Examiner* — Louise Humphrey
*Assistant Examiner* — Stephen A Perkins
(74) *Attorney, Agent, or Firm* — Wolf, Greenfield & Sacks, P.C.

(57) ABSTRACT

Certain embodiments and aspects relate to a photobioreactor including encapsulating photobioreactor units (EPU) within which a liquid medium and a gas are encapsulated. The liquid medium comprises at least one species of phototrophic or mixotrophic organism therein. The gas comprises a high concentration of carbon dioxide. Certain methods of using the EPUs for algal biomass production use automated function units.

24 Claims, 4 Drawing Sheets

PHOTOBIOREACTOR SYSTEMS AND METHODS FOR PRODUCING BIOMASS

RELATED APPLICATIONS

This application claims priority under 35 U.S.C. § 119(e) to U.S. Provisional Application Ser. No. 62/023,636, filed Jul. 11, 2014, entitled "Photobioreactor Systems And Methods For Producing Biomass", the contents of which are incorporated herein by reference in its entirety for all purposes.

FIELD OF THE INVENTION

The invention relates generally to photobioreactors and the use of photobioreactors for biomass production.

DISCUSSION OF THE RELATED ART

With continuous increases in population, sustainable food sources becomes a concern. It is predicted that meat consumption per capita will increase by more than 40% from the year 2007 to 2050 (Jelle Bruinsma, "THE RESOURCE OUTLOOK TO 2050: BY HOW MUCH DO LAND, WATER AND CROP YIELDS NEED TO INCREASE BY 2050?"; FAO Expert Meeting, 24-26 Jun. 2009, Rome), whereas the arable land per capita will decrease by 57%. Therefore, it is necessary to increase area productivity of produced product substantially to meet the projected demand.

At the same time, for meat production, when examining the feed conversion ratio (FCR), aquaculture ranks highest with a FCR ranging from 1 to 2, whereas for poultry and ruminants the FCRs are typically ranging from 2-20. Yet another advantage of aquaculture produce is the presence of high content of unsaturated fatty acids, especially DHA and EPA.

One of the primary ingredients for fish feed, the fishmeal, is derived from fish and aquaculture waste product. Annual capture rates are peaking, while farming is still increasing, and fishmeal demand is increasing at rate of 7-8% APR. Therefore, finding a suitable substitution for fishmeal is of great interest. For certain aqua species such as Salmon, not only high lipid content in feed is required, but also high content of omega-3 lipids is needed. For this type of species, fish oil may be a more important part of the feed. Aqua animals do not produce omega fatty acids by themselves. Instead, the omega fatty acids were derived from marine algae through the food chain. Additionally, as large amounts of fish oil are being used in dietary products for human consumption, the demand for fish oil substitution is even more urgent than fishmeal. To date, none of the lipids derived from land plants can replace fish oil while producing the same quality of lipid profile within farm raised aqua products.

Many substitutions for fishmeal and fish oil have been evaluated. For example, soymeal, fermented soymeal, soy protein extract, soy protein concentrate, yeast, soy oil, palm oil, krill oil, etc. Of those materials, some of them have anti-nutritional factors which inhibit growth, some are too expensive, some have lower nutrition level, and some cannot produce the same high quality meat profile as captured ones.

Microalgae biomass, on the other hand, is a promising substitution for both high protein source and high value lipid source. As mentioned above, the omega-3 fatty acid in fish is coming from microalgae. Another example is that *Spirulina* is a known protein source for fish feed which has similar amino acid profile of fishmeal, with 62-65% protein content, the same level as fishmeal. It is also important that microalgae is a single cell plant which can double itself within hours, and hence the annual productivity could be more than 10 time of that for soybean for the same footprint. Certain algae strains can also be cultivated mixotrophically, with high area productivity. Certain strains can also produce high value pigments, such as phycoprotein, carotenoids, and astaxanthin. Those pigments can be either used as feed ingredients or dietary ingredients.

In the past, algae cultivation projects have been funded extensively. For example, the U.S. Department of Energy (DOE) funded an extensive series of studies to develop renewable transportation fuels from algae since 1978 (DOE aquatic species program, 1978-1996; DOE NAABB algal biofuel consortium program, 2010-2013; DOE algae testbed and water reduction program, 2012; DOE advancement in algal biomass yield, 2013), and DARPA has invested over $60 million for algae jet fuel production in years 2008-2012. In Japan, government organizations (e.g., MITI), in conjunction with private companies, have invested over $250 million into algal biotechnology. In France, a 160 million Euro algae biofuels and byproducts program was launched in 2012. Each program took a different approach, but because of various problems addressed by certain embodiments herein, none has been commercially successful to date. Despite the technology hurdles, it is generally recognized that no matter what the product sector to be addressed, the protein part of biomass must be used as feed, to make the process commercially viable.

SUMMARY

Certain embodiments and aspects disclosed herein relate to: encapsulating photobioreactor units (EPUs); methods and systems for controlling and operating EPUs; and the uses of EPUs for algal biomass and high value product production.

In some embodiments, a system for cultivating algae includes a plurality of encapsulating photobioreactor units (EPUs) configured to float in a body of water, each EPU comprising a first portion fluidically connected to a second portion. The first portion comprises a liquid media, and the second portion comprises a gas. In addition, a handler is configured to receive each EPU, harvest at least a portion of the liquid media from each EPU, and add liquid media to each EPU.

In certain embodiments, a method of using photobioreactor units for growth of phototrophic and/or mixotrophic organisms includes inoculating a rigid encapsulating photobioreactor unit with a first liquid media, floating the EPU in a body of water, growing phototrophic and/or mixotrophic organisms within the first media in the EPU while the EPU is floating in the body of water. In addition, the method comprises removing at least a portion of the first liquid media from within the EPU, adding a second liquid media to the EPU through dilution and addition of nutrients, encapsulating the second liquid media in the EPUs with a concentration of $CO_2$ between about 4 v/v % and about 100 v/v %, placing the EPU into the body of water, and dewatering the removed first liquid media.

In some embodiments, the system comprises an EPU. In certain embodiments, the system comprises a plurality of EPUs. In some embodiments, the EPU has an internal volume of 5 L or less. In some cases, the system may be scaled by adding additional EPUs. In some embodiments, the EPU comprises a rigid material.

In certain embodiments, the system comprises a handler. In some embodiments, the handler is configured to harvest media from the EPU. In certain embodiments, the handler is configured to inncoulate the EPU. In some embodiments, the handler is configured to clean and/or disinfect the EPU. In some cases, the handler may remove and/or return an EPU to the system. In certain embodiments, the handler is configured to add and/or remove at least a portion of a liquid media and/or a gas to the EPU. In some embodiments, the handler is configured to seal an EPU (e.g., with a cap). In some cases, the handler may be a centrally located system. In some embodiments, the handler is an automated system. In certain embodiments, the system comprises one handler (e.g., the system does not require more than one handler). In some embodiments, the system comprises two or more handlers.

In some embodiments, the system comprises a body of water. In certain embodiments, the EPUs are floating in the body of water. In some embodiments, the body of water is used to maintain the temperature of the EPU. In certain embodiments, the EPUs are filled with a liquid media such that the EPUs maintain a substantially vertical alignment in the body of water.

Any of the above features can be combined with any of one or more other features. For example, in some embodiments, the system comprises a plurality of EPUs and a handler, wherein the EPUs have a volume of less than about 5 L and float in a body of water, and wherein the handler is configured to harvest and refill a liquid media and/or a gas contained within the EPU.

Other advantages and novel features will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Other advantages, novel features, and uses of the present disclosure will become more apparent from the following detailed description of non-limiting embodiments when considered in conjunction with the accompanying drawings, which are schematic and which are not intended to be drawn to scale. In the figures, each identical, or substantially similar component that is illustrated in various figures is typically represented by a single numeral or notation. For purposes of clarity, not every component is labeled in every figure, nor is every component of each embodiment shown where illustration is not necessary to allow those of ordinary skill in the art to understand the invention.

In the drawings.

DETAILED DESCRIPTION

A major obstacle for feasible commodity scale algal biomass production has been an efficient and reliable, yet cost-effective, growth system. DOE and DARPA's research were focused on selecting strains and growing in massive open ponds. To maintain the current flow in large shallow ponds, the capital input requirement is not insignificant. The energy input required to drive a man-made river is not negligible. Whereas, algae grown in open and uncontrolled environments is typically expected to produce low levels of output. Hence, the open pond technology made growing and harvesting the algae prohibitively expensive, because massive amounts of dilute algal waters required very large agitators, pumps and dewatering devices. Furthermore, in an open environment, contamination is not preventable, and toxic contaminants may prevail. This may not only lead to productivity drawbacks, but also introduce the risk that the produced material could be toxic for food or feed purposes. On the other hand, the MITI approach, with stricter land constraints, focused on very expensive closed algal photobioreactors utilizing fiber optics for light transmission. In these controlled environments, much higher algal productivity was achieved, but the algal growth rates were not high enough to offset the capital costs of the systems utilized. This type of photobioreactor generally requires significant maintenance and is not scalable. Other examples of closed photobioreactors known in the art include U.S. Pat. Nos. 2,732,663; 4,473,970; 4,233,958; 4,868,123; and 6,827,036.

Burlew (Burlew, John S. "Algal Culture: From Laboratory to Pilot Plant." Carnegie Institution of Washington Publication 600. Washington, D.C., 1961 (hereinafter "Burlew 1961")) provides an overview of several designs for algae bioreactors. The bioreactors discussed in Burlew 1961 include the use of glass tubes, open tanks, open trenches. More recently, Pulz and Scheibenbogen (Pulz O. and Scheibenbogen K. "Photobioreactors: Design and Performance with Respect to Light Energy Input," Advances in Biochemical Engineering/Biotechnology, 59:pp 124-151 (1998); hereinafter "Pulz 1998") reviewed algae photobioreactors, and Richmond (Richmond A. ed. "Handbook of Microalgal Culture—Biotechnology and Applied Phycology, Blackwell Publishing, Oxford, U K (2004); hereinafter "Richmond 2004") reviewed the general state of the art of microalgae culturing, including reactor design. Both references (Richmond 2004 and Pulz 1998) note that open systems, such as natural lakes, circular ponds, and raceway reactors are the predominate commercial technology. Open air systems used for cultivation of algae are also shown in, for example, U.S. Pat. Nos. 3,650,068; 3,468,057; and 4,217,728. Pond system variations, for example, the sloped pond design (US Pub. No. 2011/0287531 A1) and covered pond design, (U.S. Pat. Nos. 8,110,395; 8,507,264), can also be found. A hybrid pond and PBR design is also disclosed (U.S. Pat. No. 7,980,024). In this design, a sealed floating pond with cable driven internal agitator is employed, made it low in operational cost where most contaminants are excluded. Such systems, however, are still low in productivity which may be difficult to offset the capital cost.

It is lately generally recognized that in closed photobioreactor (PBR) systems, sterile in place (SIP) and clean in place (CIP) methods are required, or the PBR system will suffer contamination issues which will lead to system shut down. Michael C. Flikinger reviewed the biggest PBR failure in 1991 in Spain (Upstream Industrial Biotechnology, Volume 2, 2013). These additional needs, adding more cost to PBR systems, makes it more difficult to be cost effective. Solix Biosystems disclosed a PBR design using flexible material to form liquid flow channel immersed in water (US Pub. No. 2008/0160591 A1). Where the submersed design takes care of temperature control and structural supporting, the long flow channel makes difficult to perform CIP or SIP. Flexible material may shorten the lifetime of the channel, introducing high operational costs in long run.

In light of the requirements for PBR design discussed above, some embodiments disclosed herein include advantages such as better controlled environments, faster growth, and higher concentrations, while addressing cleaning and sterilization needs. Another advantage of certain embodiments described herein include meeting the requirements in a cost effective way, such as using automated system, and reducing the overall algal biomass production system cost (e.g., lower demand for inoculant and lower load for harvesting, etc.)

Certain embodiments of the disclosure include one or more encapsulating photobioreactor units (EPUs) for biomass production.

According to one aspect, EPUs are used for cells to grow photosynthetically or mixotrophically. In some embodiments, the EPU is a transparent container which allows light to penetrate in. In certain embodiments, the container has two major portions that are interconnected. For example, in some cases, the smaller portion is filled with media with algae cells, and the larger portion is filled with $CO_2$ rich gas. In some embodiments, the container has a cap that seals the container during normal growth. In certain embodiments, the cap can be open for EPU operations.

According to another aspect, multiple EPUs may be used for large scale algae cultivation. It may be advantageous, in some embodiments, that the EPUs are floating in a body of water, with a gas portion above a water line and a liquid media submersed under the water line, such that expensive support structures that are commonly found in PBRs can be eliminated.

According to another aspect, the EPUs are floating in the body of water. The heat absorbed from solar incidence is then passed onto the bulk water that the EPUs floating in. Due to the large heat capacity of the body of water, the temperature variation, for example, in EPUs may be limited, providing suitable physical condition for cells to grow.

According to another aspect, automated equipment (e.g., a handler) is used for operation of the EPUs. Such automated equipment may be similar to a water bottling machine with some modifications, and the primary operation may be similar to a water bottling process with some modifications. For example, during operation, the filling/discharge of EPUs, cleaning and sterilization of EPUs, and/or harvesting and re-inoculation of culture media can be performed in a central location (e.g., the handler). As will be understood by those skilled in the art, several known bottle handling machines are available and would be suitable for use as a handler.

According to another aspect, the EPUs floating in water are driven by certain mechanism (e.g., a driver) and circulation around a mixing mechanism (e.g., a mixer). The mixer may, in some cases, disturb the EPUs vigorously, to enhance the mass transfer between liquid and gas phase within EPUs. More specifically, the mass transfer here is referred to $CO_2$ transfer into media and oxygen transfer from media to gas phase. The driver may also send EPUs through the handler, at which handling is taking place.

According to another aspect, the combination of SIP and CIP for the EPUs and with the sealed EPUs during normal growth such that the entire cultivation is under contamination free conditions.

According to another aspect, special design of the EPU shape is desired, so that the liquid media portion is well spaced in the body of water such that the light utilization efficiency can be maximized and a high growth rate can be achieved.

According to another aspect, the EPUs are designed to have short light passage through culture. Advantages of short light passage include higher biomass concentration, leading to a lower amount of water handling for cultivation and for harvesting processes.

It may be advantageous, according to one embodiment, for organic carbon material to be present in the media, to allow for mixotrophic growth of the strain in media.

According to one embodiment, a photobioreactor system comprises a plurality of EPUs, handlers, drivers, mixers, and at least one body of water. In some embodiments, to initiate the cultivation, empty EPUs are firstly fed to a handler. In certain embodiments, the handler will clean and sterilize the EPUs, after which culture media which contains nutrients, water, and strains for growth will be filled. In some embodiments, the media-filled EPUs are further filled with $CO_2$ rich gas, after which the EPUs are capped to form sealed environment. In some cases, the sealed EPUs may have atmospheric pressure within the units. In some embodiments, the sealed EPUs are then released into body of water, which is open to sunlight. In certain embodiments, the EPUs floating in the body of water are driven by the driver, to reach a mixer periodically. In some embodiments, the mixer disturbs the EPUs vigorously (e.g., enhancing the mass transfer between liquid and gas phase within EPUs). In some cases, the cells growing inside EPUs may transform nutrients into biomass. After certain time, in some cases, one nutrient is spent, and the EPUs are sent to a handler, where the caps are removed, and the gas and media content are removed. In some cases, the EPUs are then cleaned and sterilized, and refilled with fresh media and gas, and the new cycle of growth will start after the EPUs are capped.

According to a another embodiment, a photobioreactor system comprises a plurality of EPUs, handlers, drivers, mixers, and at least one body of water. Multiple EPUs may be grouped into groups, in some cases, and each group may be filled with one age of culture media. In some embodiments, the EPUs that are filled with inoculants are called Stage I, and the EPUs that are filled with subculture from Stage I are called Stage II, and so on so forth. In some embodiments, for all stages before the last stage, total subculture (i.e, all the media removed from EPUs) is diluted with fresh media for next stage cultivation without removing the EPU for harvesting. In some cases, each stage may have more EPUs than previous stage. In some cases, the system may be scaled up by adding EPUs, handlers, mixers, and drivers, rather than making larger EPUs. In some embodiments, the EPUs in different stages are placed in the same one body of water. In certain embodiments, each stage will have a dedicated body of water for EPUs to floating within, and for each body of water, one or more mixers and one or more drivers will be provided. In some cases, all EPUs may be handled with one handler. In certain embodiments, for each stage, at least one dedicated handler is provided.

According to another embodiment, a photobioreactor system comprises a plurality stages of EPUs, handlers, drivers, mixers, and at least one body of water. In some embodiments, for the last stage, the media removed from EPUs can be totally harvested, and through this way the overall age of the culture can be controlled. In this operational mode, for example, fresh inoculants generated from seed bank may be used. It may be advantageous, in some embodiments, for this operation to be applied to all type of strains. For example, this operation may be favorable to genetically modified organism (GMO) as GMOs are generally retarding its integrity after certain age.

According to another embodiment, a photobioreactor system comprises a plurality stages of EPUs, handlers, drivers, mixers, and at least one body of water. In some cases, the media removed from last stage EPUs may be partially harvested, with a small portion used as inoculants for Stage I. This may be applicable to strains, in some cases, that do not retard its integrity for a long time. Many natural algae strains are suitable for such cultivation mode. Advantageously, demand for fresh inoculants is not frequently required.

According to another embodiment, a photobioreactor system comprises a plurality stages of EPUs, handlers, drivers, mixers, and at least one body of water. In some cases, growth media composition, typically with a full spectrum of nutrient elements, may be provided to the early stages. Advantageously, the growth in those stages is typically fast. In some embodiments, for the last several stages, lean media composition, typically with one or two key nutrient such as nitrogen and phosphor absent, is provided. Advantageously, secondary metabolite for high value products, such as lipids, omega lipids, pigments, antioxidants, etc., can be stimulated. In some cases, the media removed from the last stage of EPUs may be totally harvested.

According to another embodiment, a photobioreactor system comprises plurality stages of EPUs, handlers, drivers, mixers, and at least one body of water. In some cases, growth media composition, typically with full spectrum of nutrient elements, may be provided to the early stages. Advantageously, the growth in those stages is typically fast. In some embodiments, the media removed from the last stage of those early stages is partially sent to further stage, whereas the remaining media is sent back to Stage I as inoculants. In some cases, for the stages after those early stages, lean media composition, typically with one or two key nutrient such as nitrogen and phosphor absent, may be provided. Advantageously, secondary metabolite for high value products, such as lipids, omega lipids, pigments, antioxidants, etc., can be stimulated. In some cases, the media removed from the last stage of EPUs may be totally harvested.

In some embodiments, early stage EPUs are floating in one body of water with one temperature range that is suitable for growth, while later stage EPUs are floating in another body of water with a temperature range suitable for secondary metabolites production. In some embodiments, the temperature in body of water can be controlled. Non-limiting examples of temperature controlling mechanisms include heat exchange, forced evaporative cooling, and changing the EPU coverage in body of water.

According to another embodiment, a photobioreactor system comprises plurality stages of EPUs, handlers, drivers, mixers, and at least one body of water. In some embodiments, each stage may have one strain (i.e. multiple strains may present in the system, at different stages). In certain embodiments, each stage is a pure culture of a single strain, whereas the entire system is a mixture of multiple strains with growth media compositions that are suitable for each strain provided to corresponding strains. In some embodiments, with respect to one strain, the culture moves up through each stage either with single media composition throughout each stage for primary product, or with full spectrum media at early and lean media from the last stage of those early stages, for secondary product. In some cases, partial culture from the end of full spectrum media stage may be sent back as inoculants. In some embodiments, the media removed from the last stage of EPUs is completely harvested. In certain embodiments, one or more bodies of water is provided for EPUs to float within. In some cases, bodies of water have different temperatures provided for different strains and/or different products. In some embodiments, the temperature of a body of water can be controlled by multiple ways, such as using heat exchanger, forced evaporative cooling, and changing the EPU coverage in body of water. In certain embodiments, the handlers are fully cleaned and sterile each time when strain is switched to prevent cross contamination.

According to another embodiment, a photobioreactor system comprises plurality stages of EPUs, handlers, drivers, mixers, and at least one body of water. In some embodiments, EPUs in all stages except the last stage are operated in one of the embodiments mentioned above. In certain embodiments, for the last stage, a second microorganism, either an algae strain of a bacteria strain, is introduced into the media. In some cases, the EPUs in last stage may be floating in body of water, without being mixed by Mixer. Advantageously, such induced strain will help to flocculate the algae suspension and form sediments of algal biomass. In some embodiments, the biomass in the media harvested from the last stage EPUs can be easily separated using conventional equipment including filtration, centrifuge, clarifier, and/or the like.

Certain embodiments and aspects of the present disclosure relate to photobioreactor units designed to encapsulate certain amounts of gas which may have a high $CO_2$ concentration and certain amount of liquid medium comprising at least one species of phototrophic or mixotrophic organism therein, and to methods of using the photobioreactor units for algal biomass cultivation.

Figure 1:
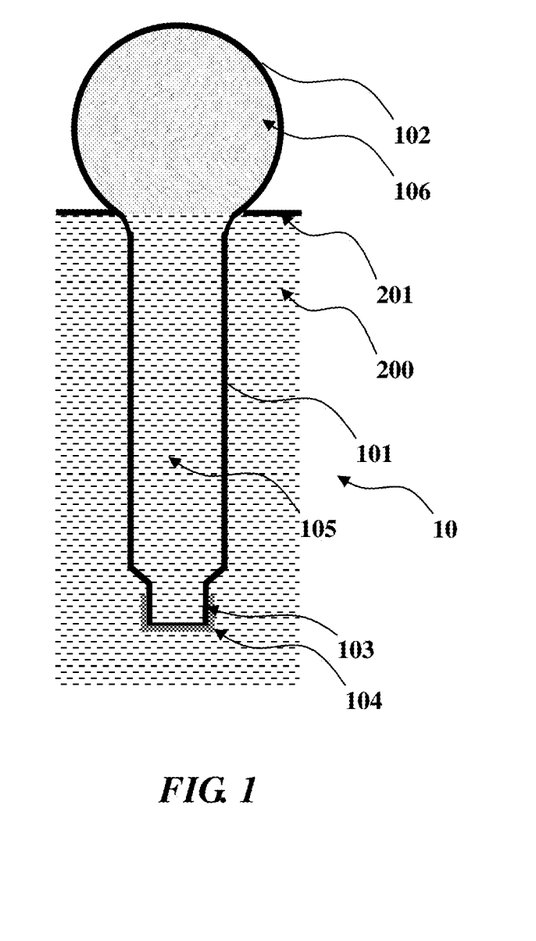
FIG. 1 is a cross sectional view of an exemplary EPU according to one aspect of the invention.

An example of an EPU 10 is shown in FIG. 1. In some embodiments, EPU 10 comprises first portion 101 comprising a liquid media and second portion 102 comprising a gas. During growth of an organism, the EPUs may float in body of water 200 vertically, with first portion 101 immersed in the body of water and second portion 102 floating above water line 201. In certain embodiments, the cultivation temperature of an EPU is determined by the temperature of the body of water. At least one port (shown as 103) may be present in an EPU to allow filling and discharge of encapsulated content. The port can be sealed by, for example, cap 104, to form an encapsulated environment. In some embodiments, liquid portion 101 is filled with liquid media 105 comprising at least one photoautotrophic or photo-mixotrophic organism. Necessary nutrients may also be provided in the media to support growth. In some cases, second portion 102 is filled with gas 106. In some embodiments, the gas may contain carbon dioxide (e.g., as carbon source for photosynthesis). Any suitable range of carbon dioxide may be used. For example, in some cases, the gas may contain a between about 4 v/v % and about 100 v/v % carbon dioxide. In certain embodiments, the gas may contain a low concentration of carbon dioxide (e.g., between about 4 v/v % and about 10 v/v %). In some embodiments, the gas may contain a high concentration of carbon dioxide (e.g., between about 90 v/v % and about 100 v/v %).

In some cases, while an EPU is floating in the body of water, the shape of the EPU is center symmetric from a top view. For example, a center symmetric shape may be a circle. Other shapes such as hexagonal, octagonal, or the like are also possible. Asymmetric shapes may be used, (e.g., with the addition of a sorting request for handlers). It may be advantageous, in some cases, when viewing the system from the side of an EPU while the EPU is floating in a body of water, that the horizontal dimension of second portion 102 may be larger than first portion 101. For example, this may create space between EPUs for liquid media, and may create a light path down to the lower points of the first portion of the EPU. The vertical dimensions for the first portion and the second portion may arbitrary. In some embodiments, the dimension of the first portion is greater than about 5 cm, or greater than about 10 cm. It may be advantageous, in some cases, for the light path to be relative short as to minimize any dark regions as algae cells have strong light extinction capability. In some embodiments, the horizontal dimension for the first portion ranges between about 2 cm and about 20 cm. In certain embodiments, the horizontal dimension of the first portion ranges between about 4 cm and about 12 cm. By varying those four dimensions, different light utilization efficiency may be obtained. This may help to optimize the cost effectiveness of the overall system.

In some cases, it may be advantageous that the time interval between handling EPUs is as long as possible, since the capital cost for handler may be dominating, and reduction in the handlers' load is beneficial. The time interval is generally determined by one limiting nutrient. For example, for photoautotrophic growth, the limiting nutrient may be $CO_2$. Therefore, in some cases, it may be desirable to fill pure $CO_2$ gas into the second portion. Advantageously, by increasing the ratio of gas/liquid volume ratio, longer residence times may be obtained. For mixotrophic growth, since organic carbon is provided as additional carbon source, the limiting nutrient may not necessarily be $CO_2$ gas. Therefore, in some cases, the ratio of gas volume to liquid volume may not be related to cost control. In some embodiments, the ratio of gas volume to liquid volume is greater than about 1:1, or greater than about 1.5:1. In some cases, the ratio of liquid volume to gas volume may be determined by a growth season and/or type of operation. Although mentioned as liquid filled portion and gas filled portion, there is no exact cut of the two portions within an EPU. That is to say, the amount of liquid and gas filled into an EPU is variable. Such variation is determined by the growth seasons and types of operation.

In some embodiments, second portion 102 has a hemispherical top (e.g., such that the EPU can be out of balance when this portion is placed on water with the first portion remaining vertical). In some cases, cap 104 may be filled with heavy materials such as steel or sand (e.g., such that once the EPU tipped over, the weight of the cap can further help the first portion immersed in the body of water align itself to the normal position shown in FIG. 1.)

In some embodiments, the EPUs comprise a transparent material. Non-limiting examples of transparent materials include glass, polycarbonate, acrylic, PETG, polypropylene, and PVC. In certain embodiments, the EPUs comprise a translucent material. Non-limiting examples of translucent materials include polyethylene (e.g., high density polyethylene), ABS, and the like. In some embodiments, the EPUs comprise a rigid material (e.g., a rigid polyethylene). It should be understood by those skilled in the art that materials generally suitable for consumer food packaging (e.g., bottled drink containers, plastic bottles, plastic bottle caps, etc.) could also be used. In some embodiments, the rigid material is of the thickness of a typical bottled drink container (e.g., a soda bottle)

In certain embodiments, the EPU has a vertical dimension ranging from about 10 to about 100 cm inclusive. In some embodiments, the EPU has a horizontal dimension ranging from about 1 cm to about 20 cm inclusive. In certain embodiments, the EPU has a volume ranging from about 100 mL to about 20 L inclusive. In some embodiments, the EPU has a volume ranging from about 1 L to about 5 L inclusive.

Non-limiting examples of photosynthetic or mixotrophic organisms include algae and cyanobacteria (e.g., in unicellular or multi-cellular form). Generally, organisms that are capable of growth in a liquid media can be used for biomass production. Non-limiting examples of organism strains include *Chlorella, Chlamdomonas, Chaetoceros, Spirulina, Dunaliella, Porphyridum, Haematococcus, Nannochloropsis, Pavlova, Isochrysis, Thalassiosira*, and *Tetraselmis*.

In some embodiments, the liquid media comprises macro nutrients and micro nutrients and is used for cultivation and biomass production. In certain embodiments, the macro nutrients comprise at least one source for nitrogen, phosphate, and/or potassium. In some embodiments, the macro nutrients comprise at least one organic carbon (e.g., for mixotrophic growth). Non-limiting examples of macro nutrients include organic carbon include sugar, glucose, fructose, acetic acid, citric acid, and glycerin. In certain embodiments, the micro nutrients include at least one source for iron, magnesium, calcium, boron, cobalt, manganese, zinc, and/or other trace metals. In some cases, chelating reagents, such as EDTA, may be provided to stabilize the metals. For certain organism strains, multivitamins may be provided for growth. In some embodiments (e.g., for marine strains), the liquid media has high salinity (e.g., greater than about 3%). In certain embodiments (e.g., for fresh strains), the liquid media has low salinity (e.g., less than about 0.5%).

In certain embodiments, the biomass concentration (e.g., the total mass of organisms and organic materials) in the encapsulated liquid media ranges from about 0.1 g/L to about 20 g/L inclusive (e.g., for photosynthetic growth). Such ranges may be a result of short light passage and sterile operation. In some embodiments, the biomass concentration ranges from about 1 g/L to about 10 g/L inclusive, or from about 2 g/L to about 8 g/L inclusive. In some cases (e.g., during mixotrophic growth), it may be advantageous for the biomass concentration to be greater than or equal to about 100 g/L. Such ranges may be a result of mutual shading effect between cells which may not slow down growth. The cell concentration at harvesting is generally higher than that from open pond system, which is typically less than about 0.5 g/L, significantly reducing the load for harvesting.

In some cases, the growth rate in the EPUs may range from about 0.05 to about 25 g/L per day inclusive, depending on the type of growth. In some cases, based on mass balance and growth rate, the time intervals between handling for an EPU may range from about 0.5 days to about 15 days inclusive (e.g., variable as determined by temperature, solar incident, and other factors). When projected to the productivity based on footprint, the productivity may range between about 15 g/m$^2$ per day and about 200 g/m$^2$ per day (e.g., depending on the type of cultivation, the growth rate, and the packing density of EPUs in body of water).

Figure 2:
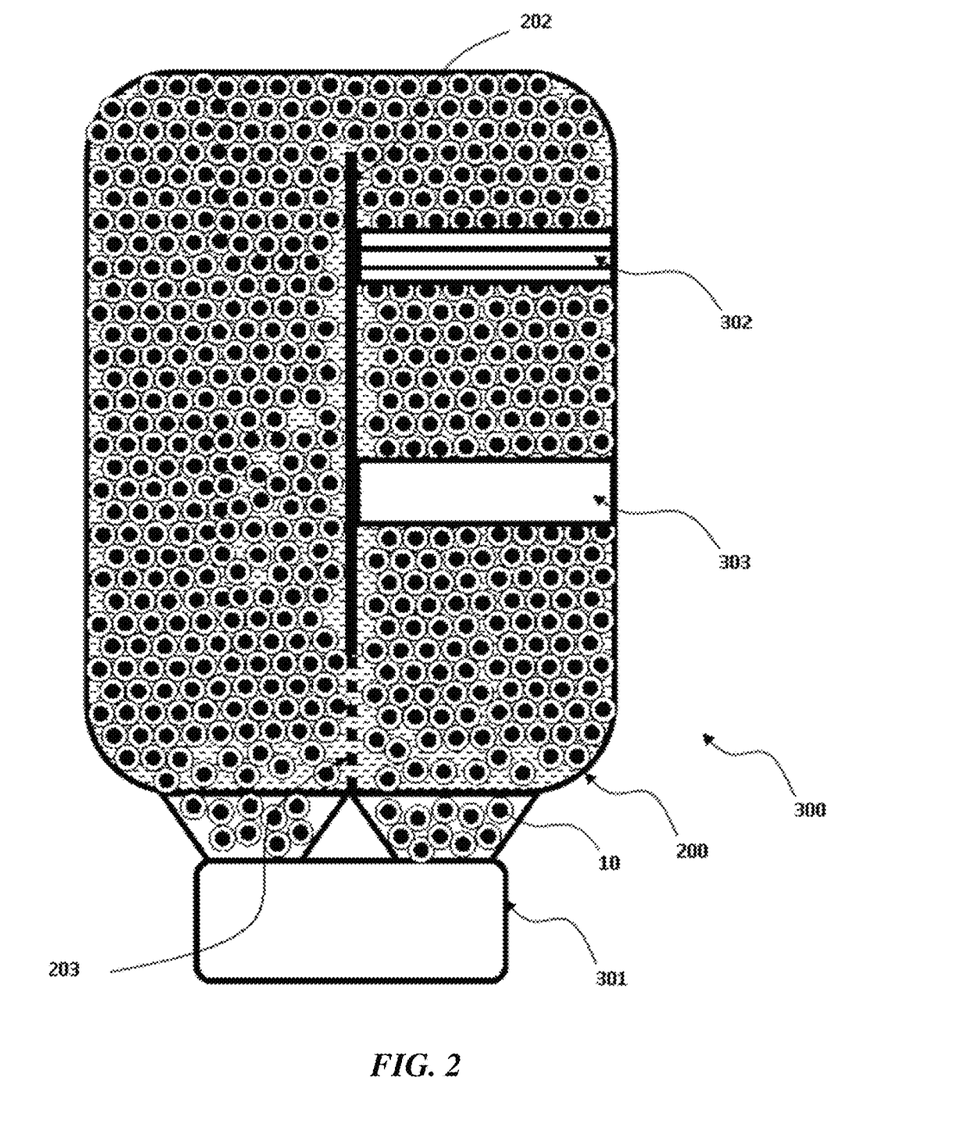
FIG. 2 is a diagram of an exemplary photobioreactor system according to one embodiment of the invention.

According to one embodiment, cultivation system 300 comprises at least one handler, one mixer, one driver, one body of water, and a plurality of EPUs, as illustrated in FIG. 2. In FIG. 2, EPUs 10 are floating in body of water 200. The water depth in the body of water may be at least deep enough to allow the EPUs to float without scrubbing the bottom (e.g., the water depth is larger than the vertical dimension of the first portion of an EPU). In the body of water, a baffle plate 202 may be used to create a circulation movement of the EPUs. Driver 302 drives the EPUs to travel in one direction. The EPUs reach mixer 303 during drifting. In some embodiments, it may be advantageous to mix the EPUs to enhance mass transfer between gas and liquid, satisfying a mass balance requirement for growth. A mixer 303 is used in some embodiments to vigorously mix the gas and liquid encapsulated in the EPUs. Non-limiting examples of mixing includes vibrating of EPUs, splashing EPUs out of water, centrifugal rotating of EPUs, etc.

Figure 3:
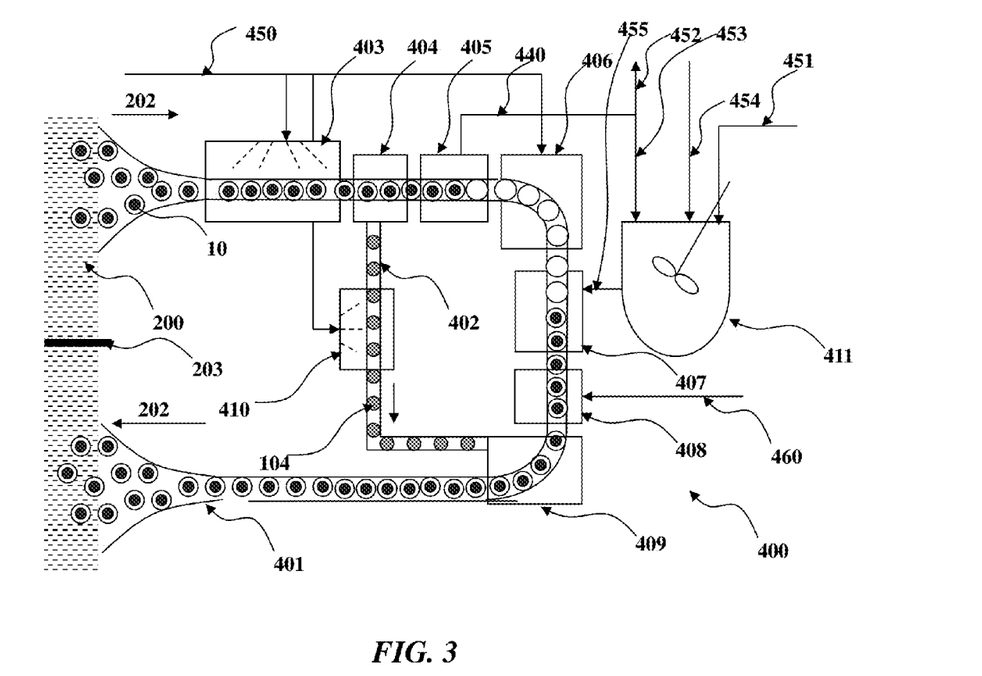
FIG. 3 is a diagram of an exemplary handler system according to one embodiment of the invention.

Once the EPUs reach their residence time, which may be determined by one limiting nutrient in the EPUs, another diverting baffle plate 203 may be provided, to guide the EPUs to a handler 400. In some cases, a handler is an integrated automated system which processes the EPUs. In certain embodiments, the handler comprises one or more process units. FIG. 3 shows an exemplary handler 400.

As illustrated in FIG. 3, handler 400 includes at least one conveyer system 401 which transfers the EPUs 10 throughout the system. Arrow 202 shows a direction that the EPUs may be transferred. In some embodiments, the EPUs are transferred through several process units, as described herein, to complete the handling process before returning to body of water 200 for cultivation. For example, the outside surface of EPUs may be cleaned and disinfected in a cleaning process unit 403, followed by removal of cap 104 in a process unit 404. In some cases, the caps may be collected from process unit 404 and transferred through conveyer 402, during which the caps may be cleaned and disinfected by a process unit 410 and delivered to a process unit 409. The EPUs without caps then may be passed through a process unit 405 where the containing media 440 is removed from the EPU. In some embodiments, the empty EPUs then are passed through a process unit 406, in which water jets are used for cleaning and sterilization. In some cases, the sterilized EPUs then may be filled with fresh media in a process unit 407, charged with high concentration gas in a process unit 408, and then capped in process unit 409. The capped EPUs then may be sent back to body of water 200 for growth.

In some embodiments, a cleaning and/or disinfection solution 450 is provided to process units 403, 406, and 410. In some cases, it may be advantageous to maintain process units 404-411 under sterile conditions (e.g., by using a disinfection solution, gamma rays, UV light, or high pressure steam) to keep the cultivation sterile. In some embodiments, partial culture (e.g., a portion of a harvested stream) of the removed media 440 may be removed from system as harvesting 452. In certain embodiments, any remaining media 453 can be introduced into a stir tank, in which the media is diluted and well mixed with fresh sterile nutrient 454.

While the system shown in FIG. 3 may use removed media from EPUs for inoculant, shown as remaining media 453, one skilled in the art would readily understand that it would be possible that all the removed media be harvested. In some embodiments, fresh inoculant, shown as 451, may be added. In certain embodiments, (e.g., during operation) fresh inoculant is not required to be added for a substantial period of time. For example, the time interval between introducing fresh inoculant may range from about 5 days to about 180 days inclusive, or any other suitable time interval.

Non-limiting examples of disinfection solutions include chlorine solution (e.g., bleach), alcohol, ozonated water, hydrogen peroxide, or ethylene oxide. In some embodiments, radiation sources such as UV light or gamma rays may be used for disinfection.

While body of water 200 is illustrated in FIG. 2 as arranged in rectangular shape, any suitable shape may be employed to form the body of water. In some embodiments, as shown in FIG. 2, the body of water may be entirely filled with EPUs. It may be advantageous, in certain embodiments (e.g., when a lower temperature is required for secondary metabolite product accumulation such as lipid formation) that EPUs may be scattered in the body of water (e.g., the body of water is partially filled with EPUs) such that more evaporation surface area is available and a lower temperature in the body of water may be obtained. Typically, tight packing for round shape objects with the same diameter in a plane covers 87% of surface area. By varying the packing ratio, i.e., from 0-87%, different ratios of evaporation surface area vs. volume of water in body of water may be obtained. Such variation may be used to modulate the evaporation rate from body of water, and hence control the temperature of the cultivation. In some cases, it may be advantageous to use a submerged heat exchanger with an external heating or cooling source to gain better control of the temperature.

FIG. 2 demonstrates the use of function units (e.g., drivers, mixers, handlers). For example, one driver, one mixer, and one handler may be used during cultivation. However, one skilled in the art will understand that the system may comprise more than one of a driver, more than one of a mixer, and/or more than one of a handler. In some embodiments, more than one body of water can be used to host the EPUs. In certain aspects, an integrated function unit that combines one or more systems, as described herein, may be used. For example, in some cases, the driver and the mixer may be combined as one unit. In certain embodiments, one unit combines all the functions of driving, mixing, and handling.

Any variation from the figures discussed above, e.g., EPU size and shape, water body shape and depth, number of function units, etc., can be applied to the embodiments discussed hereafter.

Figure 4:
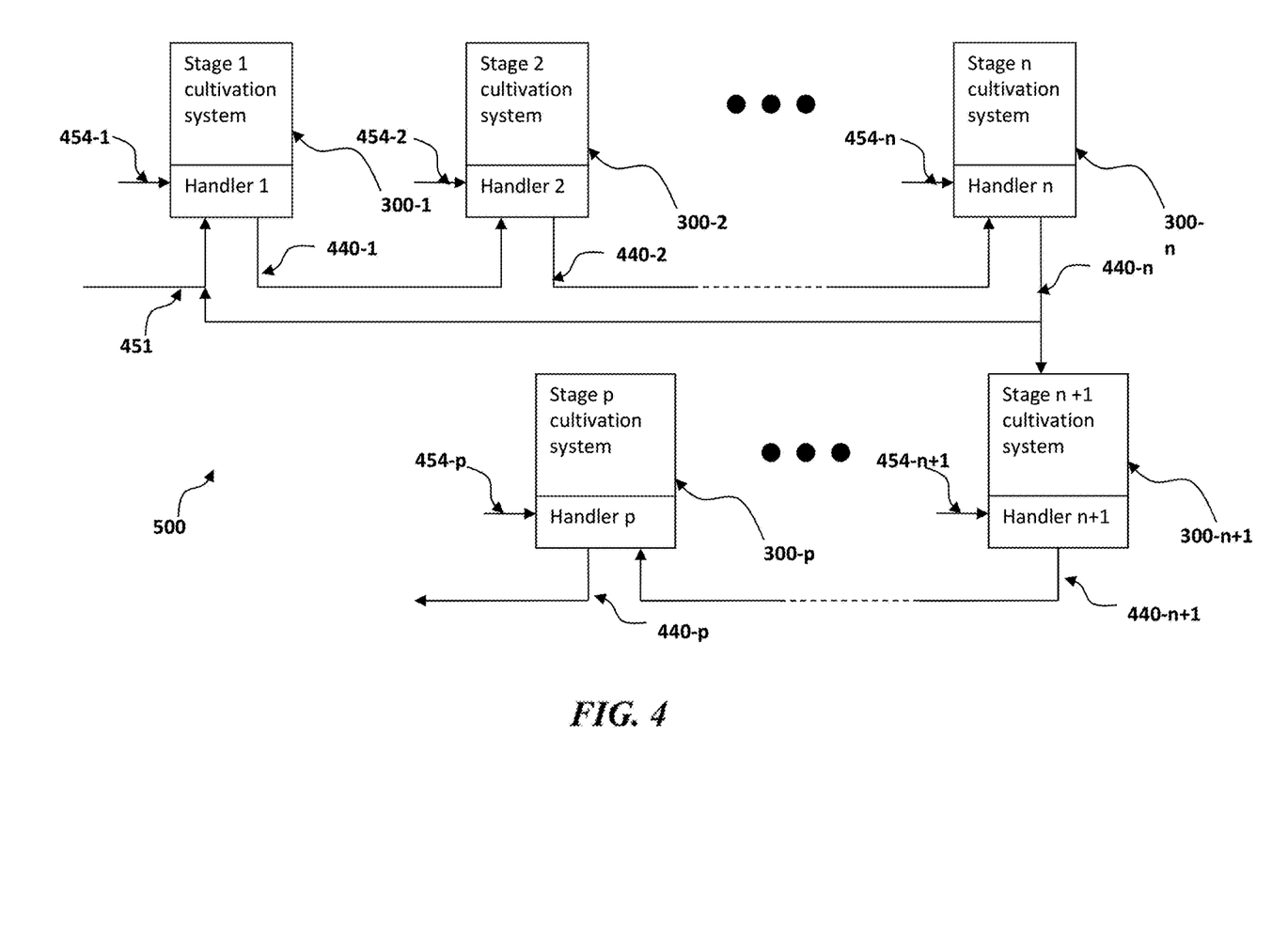
FIG. 4 is a diagram of an exemplary multistage photobioreactor system according to certain embodiments of the invention.

In certain embodiments, a photobioreactor system comprises a plurality of stages (shown as 300-$x$ ($x$=1, 2, . . . p) in FIG. 4). In some embodiments, each stage constitutes a number of EPUs floating in body of water, operated by at least one driver, one mixer, and one handler. As illustrated in FIG. 4, in stage i, media removed from the EPUs by handler (440-$i$) and sent to the subsequent stage (i+1), in which the media is diluted with fresh nutrients (454-$i$+1) and filled into EPUs for the cultivation in stage i+1.

In some embodiments, the shape of the EPU is identical in each stages. In certain embodiments, the number of EPUs in each stage is constant. In some embodiments, the number of EPUs increases in each subsequent stage (e.g., as a result of growth).

In some cases, for each stage, the function units may be dedicated to that stage. In some embodiments, several stages share the same set of function units. Each stage may have a dedicated body of water, and it is also possible that one body of water hosts multiple stages.

In certain embodiments, a photobioreactor system (as illustrated in FIG. 4) is applied for primary algal biomass production (e.g., for protein rich algal biomass production). In some embodiments, the system ends at stage n. In one embodiment, a portion of the harvested stream 440-$n$ can be recycled for inoculant, whereas the majority of the stream 440-$n$ will be sent to a harvesting device to separate the biomass from water. In another embodiment, fresh inoculant 451 is provided as regular basis, and no recycling of 440-$n$ is required. In yet another embodiment, 451 is provided occasionally and combined using 440-$n$ and 451 as inoculant, as described previously. In some cases, a full spectrum of nutrients 454-$i$ may be supplied to each stage.

According to another embodiment, a photobioreactor system, such as illustrated in FIG. 4, may be used for secondary metabolite production (e.g., for algal oil production). In some embodiments, the system ends at stage p. In certain embodiments, a first portion of harvested stream 440-$n$ can be recycled for inoculant, whereas a second portion of stream 440-$n$ will be sent to the following stage n+1. In some cases, fresh inoculant 451 is provided as regular basis, and no recycling of 440-$n$ may be required. In some embodiments, inoculant 451 is provided occasionally and combined using stream 440-$n$ and inoculant 451, described previously. In some cases, a full spectrum of nutrients 454-$i$ may be supplied to each stage between 1 to n. For example, in stage n+1 and thereon, media comprising reduced nutrient may be provided to each stage. Non-limiting examples of reduced nutrients include nitrogen, phosphorus, or silica, depending on the strains being cultivated. In some embodiments, the body of water temperature for stage n+1 to stage p can be controlled. For example, growth temperature in stage 1 to stage n may range between about 20 and about 40° C., and/or the stressing stage n+1 to p may range between about 15 and about 25° C. It may be advantageous, in some embodiments, that the cells in such stages are stressed, stimulating a secondary metabolism pathway, and increasing the yield of target intracellular product. In certain embodiments, harvested media 440-$p$ is sent to a harvesting device to separate the biomass from water.

One advantage of using a sterile environment for secondary metabolite production is that during the stressed phase (between stage n+1 and stage p), the biomass increases as more carbon is assimilated into cells. Generally, in open or non-sterile environments, the total biomass concentration for the cultivated strains would be expected to decrease as a result of contamination. Such decrease may reduce the overall productivity of the system by 20-80%, and may lead to cultivation collapse. Embodiments disclosed herein offer both high productivity and high reliability, making systems cost effective.

Since multiple strains are used, to prevent cross contamination, the transfer between stages may be scheduled in a batch wise fashion. For example, the sterilized mixing tank in stage n+1 may receive removed media from stage n. Once finished, the media may be diluted with nutrients and used to fill EPUs in stage n+1. Upon finishing the filling, the mixing tank in stage n+1 may be cleaned and sterilized, and is ready to receive another batch of removed media from stage n. This way, isolation between stages with different strains is provided, and hence cross contamination is prevented.

In some embodiments, at stage p, together with stream 454-$p$, a secondary microorganism (e.g., a polysaccharide producing algae such as Porphyridium) is introduced into the culture. Due to the stressed environment, transparent extracellular polysaccharide (TEP) may be produced, as a natural bio-flocculent. Generally, TEP will help coagulate all the algal biomass to form large particulates which can be easily separated from water.

In some embodiments, the harvesting device described herein is an ultrafiltration device or a centrifuge. In certain embodiments, the harvesting device uses chemical flocculation or bio-flocculation. In some embodiments (e.g., when bio-flocculent is used), the harvesting device is a rotating drum filtration, a clarifier, or a liquid cyclone (e.g., for water separation). In some cases, once the bulk water is removed, the biomass may be further treated to yield end products. In some embodiments, further treatment of end products include drying, extraction, and further cleanup processes. In general, since the biomass concentration harvested from EPU system is usually high (greater than about 3 g/L), much less load on water separation is expected. When chemical flocculent is used, the dosage may be much lower due to the same high biomass concentration reason. In some cases, physical treatment to induce flocculation, such as electromagnetic field and variable frequency radio wave may be applied for forming large particulates.

In some embodiments, the photobioreactor systems described herein are used for algal biomass production. The produced algal biomass can be used, for example, as feedstock for feed, dietary nutrition, food, anti-oxidant, dietary lipid, biofuel, and/or other products. In some cases, harvested algae stream 440 (referring to FIG. 4) may be used as inoculant for another type of algae cultivation system, such as open pond or tubular photobioreactor.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention.

In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood, unless otherwise indicated, to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Any terms as used herein related to shape, orientation, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A method of using a cultivation system and photobioreactor units for sterile growth of phototrophic and/or mixotrophic organisms, the cultivation system comprising a handler, the method comprising:
    inoculating a first liquid media into a rigid encapsulating photobioreactor unit (EPU);
    adding carbon dioxide into the EPU;
    after adding carbon dioxide, sealing the EPU;
    floating the sealed EPU in a body of water;
    growing phototrophic and/or mixotrophic organisms within the first media in the EPU while the EPU is floating in the body of water;
    after growing, removing the EPU from the body of water using the handler;
    with the EPU removed from the body of water, and with the first liquid media inside the EPU, disinfecting an outer surface of the EPU;
    opening the disinfected EPU;
    after opening the disinfected EPU, removing at least a portion of the first liquid media from within the EPU with the EPU removed from the body of water;
    after removing at least a portion of the first liquid media, adding a second sterile liquid media to the EPU through dilution and addition of sterile nutrients;
    after adding the second sterile liquid, sealing the EPU;
    placing the sealed EPU including the second sterile liquid into the body of water; and
    dewatering the removed first liquid media.

2. The method of claim 1, further comprising drying remaining biomass in the removed first liquid media.

3. The method of claim 1, wherein adding carbon dioxide to the EPU comprises adding a gas with between about 4 v/v % and about 100 v/v % of carbon dioxide to the EPU.

4. The method of claim 1, wherein adding carbon dioxide to the EPU comprises adding a gas with between about 90 v/v % and about 100 v/v % of carbon dioxide to the EPU.

5. The method of claim 1, further comprising mixing the first liquid media with a gas contained in the EPU.

6. The method of claim 1, further comprising removing the first liquid media and adding the second liquid media at a single processing facility.

7. The method of claim 1, wherein the nutrients comprise at least one organic material for mixotrophic growth.

8. The method of claim 1, further comprising adding carbon dioxide to the EPU after adding the second liquid media.

9. The method of claim 1, further comprising, after removing at least a portion of the first liquid media from within the EPU, removing all liquid from within EPU, cleaning and sterilizing the EPU, and reinoculating the EPU for growth.

10. The method of claim 1, comprising vigorously mixing the liquid and gas encapsulated in the EPU.

11. The method of claim 1, wherein the EPU floating in the body of water maintains a vertical alignment.

12. The method of claim 1, wherein the EPU comprises a first portion comprising the liquid media and a second portion comprising a gas.

13. The method of claim 12, wherein the first portion is immersed in the body of water and the second portion floats above the body of water.

14. The method of claim 12, wherein a horizontal dimension of the second portion is larger than a horizontal dimension of the first portion.

15. The method of claim 14, wherein the horizontal dimension of the first portion is between about 2 cm and about 20 cm.

16. The method of claim 12, wherein a ratio of gas volume to liquid volume is greater than about 1:1.

17. The method of claim 12, wherein the second portion has a hemispherical top such that the EPU is out of balance when the second portion is placed on the body of water, with the first portion remaining vertical.

18. The method of claim 11, wherein the EPU comprises a cap on the first portion such that the cap maintains the vertical alignment of the EPU.

19. The method of claim 1, wherein the EPU has a vertical dimension of between about 10 cm and 100 cm inclusive.

20. The method of claim 1, wherein the handler is configured to harvest at least a portion of the liquid media from the EPU.

21. The method of claim 1, wherein the handler is configured to clean and/or disinfect the EPU.

22. The method of claim 1, wherein the handler is configured to add and/or remove at least a portion of a liquid media and/or a gas to the EPU.

23. The method of claim 1, wherein the handler is configured to seal the EPU.

24. The method of claim 1, wherein the handler is an automated system.

* * * * *